United States Patent [19]
Uchiyama et al.

[11] Patent Number: 5,726,565
[45] Date of Patent: Mar. 10, 1998

[54] COULOMETRIC ANALYSIS METHOD AND A DEVICE THEREFOR

[75] Inventors: Shunichi Uchiyama, Fukaya; Takeshi Sato, Toki; Hirofumi Akano, Handa; Yoshiya Kawamura, Konan; Masahiro Fukaya, Aichi-ken; Hiroaki Ebisuya, Tokai; Ko Furukawa, Nagoya; Kazuyo Kajino, Toyoake; Sumio Akita, Nagoya, all of Japan

[73] Assignee: Nakano Vinegar Co., Ltd., Japan

[21] Appl. No.: 511,476

[22] Filed: Aug. 4, 1995

Related U.S. Application Data

[63] Continuation of Ser. No. 145,445, Oct. 28, 1993, abandoned.

[30] Foreign Application Priority Data

| Oct. 28, 1992 | [JP] | Japan | 290156 |
| Feb. 19, 1993 | [JP] | Japan | 30928 |
| Jul. 1, 1993 | [JP] | Japan | 163606 |
| Sep. 7, 1993 | [JP] | Japan | 222527 |

[51] Int. Cl.$^6$ ................................................ G01N 27/26
[52] U.S. Cl. ............................ 324/94; 204/415; 324/425
[58] Field of Search .................... 324/94, 425; 204/407, 204/415; 429/9, 154

[56] References Cited

U.S. PATENT DOCUMENTS

| 4,005,002 | 1/1977 | Racine et al. | 204/415 |
| 4,029,563 | 6/1977 | Binder et al. | 204/432 |
| 4,225,410 | 9/1980 | Pace | 204/407 |
| 4,374,186 | 2/1983 | McCartney et al. | 429/154 |
| 4,400,242 | 8/1983 | Albery et al. | 204/415 |
| 4,738,765 | 4/1988 | Cortina et al. | 204/415 |
| 4,839,020 | 6/1989 | Yamaguchi et al. | 204/415 |
| 4,867,860 | 9/1989 | Siddiqi et al. | 204/418 |
| 4,938,860 | 7/1990 | Wogoman | 204/415 |
| 5,133,856 | 7/1992 | Yamaguchi et al. | 204/415 |
| 5,183,712 | 2/1993 | Beldock et al. | 429/9 |
| 5,443,701 | 8/1995 | Willner et al. | 204/415 |

FOREIGN PATENT DOCUMENTS 61-156142   7/1986   Japan .

OTHER PUBLICATIONS

Buchert, J., Apr. 1991, "A xylose-oxidizing membrane-bound aldose dehydrogenase of *Gluconobacter oxydans* ATCC 621," J. of Biotechnology, 18:103–113.

Ameyama, et al., 1982. (month unavailable) "Aldehyde Dehydrogenase from Acetic Acid Bacteria, Membrane-Bound," Methods in Enzymology, 89:491–497.

Ameyama, et al., Apr. 1985, "Solubilization, Purification and Properties of Membrane-bound Glycerol Dehydrogenase from *Gluconobacter industrius*," Agric. Biol. Chem., 49(4):1001–1010.

Shinagawa, et al., (month unavailable) 1982, "D–Sorbitol Dehydrogenase from *Gluconobacter suboxydans*, Membrane-Bound," Methods in Enzymology, 89:141–145.

Davidson, V., (month unavailable) 1993, "Methylamine Dehydrogenase," Principles and Applications of Quinoproteins, Chpt. 5:73–95.

(List continued on next page.)

*Primary Examiner*—Ernest F. Karlsen
*Attorney, Agent, or Firm*—Pennie & Edmonds

[57] ABSTRACT

The present invention provides a rapid coulometric analysis for the quantitative determination of a sample substance wherein the coulometric analysis has high reproducibility without any application of voltage, etc., from an outside source, as well as a galvanic cell and a device for use in said coulometric analysis. According to the present invention, a wide variety of components can be analyzed by selection of electroactive substance introduced into the galvanic cell. The present invention enables a simple and easy analysis for food components such as glutamic acid, ascorbic acid, etc., water quality such as COD, etc.

18 Claims, 7 Drawing Sheets

OTHER PUBLICATIONS

Barrett, et al., 15 Jul. 1984, "Acetaldehyde formation by mitochondria from the free-living nematode *Panagrellus redivivus*," J. Biochem., 221–:535–540.

Ameyama, et al., Feb. 1981, "D–Fructose Dehydrogenase of *Gluconobacter industrius*: Purification, Charaterization, and Application to Enzymatic Microdetermination of D–Fructose," J. Bacteriology, 145:814–823.

Matsushita, et al., Apr. 1989, "Reactivity with Ubiquinone of Quinoprotein D–Clucose Dehydrogenase from *Gluconobacter suboxydans*," J. Biochem., 105:633–637.

Shuppan, Mar. 31, 1990, "Annotation in the hygenic test method," Pharma. Soc. of Japan, pp. 310–313 (translation provided).

Van Der Schoot, et al., "Coulometric Sensors, The Application of a Sensor–Actuator System for Long–Term Stability in Chemical Sensing," Sensors & Actuators, vol. 13, No. 3, Mar. 1988, 251–262.

Sectional drawing of galvanic cell 1

COULOMETRIC ANALYSIS METHOD AND A DEVICE THEREFOR

CROSS-REFERENCE TO RELATED APPLICATION

The present invention is a continuation-in-part of U.S. application Ser. No. 08/145,445 filed on Oct. 28, 1993, the entire disclosure of which is incorporated herein by reference.

FIELD OF THE INVENTION

The present invention relates to a coulometric analysis method (self-driven coulometry) for the quantitative determination of a sample substance by cell reaction, as well as a galvanic cell and a device used for said method.

BACKGROUND OF THE INVENTION

For the quantitative determination of a sample substance, conventional electroanalysis using electrolysis involves measuring electrical changes occurring in a reaction (e.g., oxidation, reduction, etc.) of the substance under application of constant voltage or current, and in recent years, electrically conductive porous electrodes have been applied to such analysis.

Conventional electroanalysis using ion electrodes is a method in which an ion passing through a separating membrane is detected and in which an equilibrium potential between ions resulting from a sample substance and an electrode membrane is electrically measured by each electrode immersed as a detector in a sample solution. Another conventional electroanalysis using conductive porous electrodes is a method in which a sample is directly electrolyzed in a detection chamber with a conductive porous substance impregnated with an electrolyte, as described, for example, in Japanese Published Unexamined Patent Application 195,358/89. According to this patent application, however, electrical energy should be supplied from the outside, and a long period of time is required for the stabilization of the measurement device.

Conventional analysis by a reaction via a mediator makes use of a reaction e.g. from nicotinamide adenine dinucleotide (NAD) to reduced nicotinamide adenine dinucleotide (NADH) by dehydrogenase. For such a method, a glutamic acid assay kit (manufactured by BMY Co., Ltd.), for example, is commercially available for the quantitative determination in colorimetry of glutamic acid by glutamate dehydrogenase.

However, the aforesaid electroanalysis by ion electrodes have problems such as a long measurement time due to a slow rate of ion transfer through a separating membrane and a slow response rate of reaching equilibrium, etc., and troublesome procedures such as the step of washing required after each measurement, etc.

The above electroanalysis by electrolysis also has a problem. Electrolysis of a sample substance needs constant voltage or current from an external power source. Such application of voltage, however, causes the electrodes to be in a nonequilibrium state where so-called "capacitative current" occurs. Therefore, every time voltage is applied, a long stabilization time is required for measurement by electrolysis. Another problem is that the device should be made complex because of the necessity of constant voltage or current generating units, etc.

Furthermore, the above-mentioned measurement by enzyme reaction via a mediator requires the troublesome procedures of forming e.g. NADH with an enzyme, then reacting it with diaphorase, etc., and measuring its absorbance. There are also practical problems: e.g., a refrigerator is required for storage of enzyme, etc., and a sensor intended for use at room temperature cannot be used for enzyme. In addition, it is not possible to accurately determine the absorbance where a colored substance is present in the sample.

SUMMARY OF THE INVENTION

The object of the present invention is to solve the above problems in the conventional methods and provide a coulometric analysis method for the quantitative determination of a sample substance by cell reaction, as well as a galvanic cell and a device used for said method, which does not require electrical energy such as voltage, current, etc., from an external power source and enables the rapid determination of a sample substance.

To accomplish the above object, the present inventors have made extensive research and discovered that a potential difference (electro chemical potential difference) occurs between working and counter electrodes in oxidoreduction between a component of working electrode and a sample substance where the electrical quantity generated by the potential difference is closely related to the amount of the sample substance, and that the reaction can proceed spontaneously and rapidly by selecting suitable components for the electrodes.

That is, the present invention relates to a method of coulometric analysis for the quantitative determination of a sample substance, wherein at least one of voltage, current, and electrical quantity occurring between electrodes is measured without any application of voltage from the outside, with a galvanic cell having a working electrode containing a sample substance, a counter electrode containing an electroactive substance, a material being located in an adjoining region of both the electrodes and permitting ions to pass therethrough. The words "electroactive substance" mean a chemical species participating in discharge reaction to give electromotive force as an electrochemical active species.

The present invention further relates to a method for coulometric analysis of glutamic acid, which comprises using said galvanic cell with NADH or a derivative thereof as an indicator.

In addition, the present invention relates to a method for coulometric analysis of chemical oxygen demand (COD), which comprises using potassium permanganate as an indicator and said galvanic cell with the working electrode impregnated with an electrolyte and the counter electrode impregnated with hexacyanoferrate (II) ion as electroactive substance.

Furthermore, the present invention is directed to a method for coulometric analysis of COD, which comprises using potassium permanganate as an indicator and said galvanic cell with the working electrode impregnated with an electrolyte and the counter electrode impregnated with hexacyanoferrate (II) ion and hexacyanoferrate (III) ion as electroactive substance.

Finally, the present invention is concerned with a method for coulometric analysis of ascorbic acid, which comprises using said galvanic cell with the working electrode impregnated with an electrolyte and/or 3,7 bis(dimethylamino) phenothiazine-5-ium chloride and the counter electrode impregnated with hexacyanoferrate (III) ion as electroactive substance.

Figure 1A:
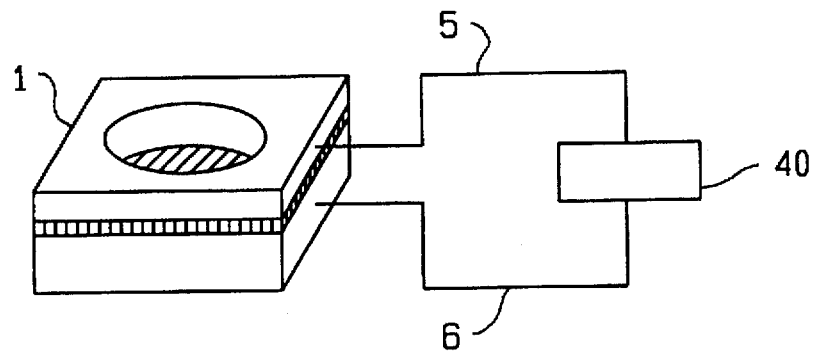
FIG. 1 is a schematic drawing of the device used in the present invention.

Symbol
1: galvanic cell.
2: working electrode.
3: counter electrode.
4: separating membrane.
5, 6: current collection electrode wires.
7: upper component.
8: lower component. upper felt.
10: lower felt.
11, 12: packing.
13: fixing screw with collar.
14: cap.
15, 16: electrode terminal.
17: bottom lid.
18, 19: sealing hole.
20: penetrating hole.
21, 22: concave parts.
23: liquid-supplement hole.
25: screw.
40: coulometer.
42: cutout part.
43, 44: terminals.
45: electric power switch.
46: start button.
47: selection button.
48: indication part.

DETAILED DESCRIPTION OF THE INVENTION

In the present invention, the above galvanic cell comprises a working electrode made of a hydrophilic and conductive material impregnated with an electrolyte (in case the sample is an electroactive substance) or with an electrolyte and/or a mediator (in case the sample reacts electrochemically with a mediator to form an electroactive substance); an upper Component provided with a penetrating hole including said working electrode, with the side having an electrode terminal joined to said working electrode; a counter electrode made of a hydrophilic and conductive material impregnated with an electroactive substance; a lower component provided with a concave part receiving said counter electrode, with the side having an electrode terminal joined to said counter electrode and the bottom having a liquid-supplement hole; a lid component for closing said liquid-supplement hole; an ion-permeable separating membrane located between said upper and lower components; and a fixing screw with collar, being fitted to said penetrating hole in said upper component and being pressed on said working electrode. The conductive material used for said working electrode may be provided on its periphery with a water-absorptive material such as a filter paper, so that discharging occurs rapidly owing to rapid dispersion of a solution into the working electrode, and the working electrode can be successively used without being replaced by a new working electrode, owing to absorption of an excess amount of a sample solution into the water-absorptive material.

This galvanic cell is provided with a current integration means, an indication part, an analysis item selection part, a start button for initiation of current integration by said current integration means, and an arithmetic means of converting integrated electrical quantity into a substance amount which is indicated in said indication part. Quantitative analysis can be easily effected by detachably inserting a pair of electrode terminals of the galvanic cell into a pair of terminals of the electroanalyzer. The indication part can indicate integrated electrical quantity directly without calculation.

The galvanic cell and electroanalyzer of the present invention are preferably used for the analysis of NADH, ascorbic acid and COD using an indicator such as potassium permanganate.

The present method is based on a coulometric analysis for the quantitative determination of a sample substance (i.e., an electroactive substance or a chemical species which reacts with a mediator to form an electroactive substance) comprising measurement of the electrical energy discharging in a short time from cell reaction of said sample substance. Hence, the present method completely differs in principle from a conventional method for quantitative determination where a sample is electrolyzed with electrical energy from an external power source.

In the present invention, the working electrode is an electrode containing said sample substance, and the working electrode can be impregnated with an electrolyte and/or a mediator. The electrode solution may be any electrolyte, for example, a solution of hydrochloric acid, sulfuric acid or potassium chloride, or phosphate buffer. The mediator includes e.g. 5-methylphenazinium methyl sulfate (phenazine methosulfate), 1-methoxy-5-methylphenazinium methyl sulfate (methoxyphenazine methosulfate), 9-dimethylamino benzo [α] phenoxazine-7-ium chloride (Meldola blue) or 3, 7bis (dimethylamino) phenothiazine-5-ium chloride (methylene blue) and salts thereof.

The counter electrode is an electrode containing an electroactive substance such as hexacyanoferrate (III) ion and/or hexacyanoferrate (II) ion. Such ions can be used in the form of a salt solution such as potassium hexacyanoferrate (III) and/or potassium hexacyanoferrate (II) dissolved in an electrode solution.

The substance located in an adjoining region of the electrodes and permitting ions to pass therethrough may be any substance which allows ions to pass therethrough while preventing direct mixing of the substances contained in the electrodes. Examples are an ion-exchange membrane for use as a separating membrane, and agar gel containing an electrolyte for use as a salt bridge, etc.

In the present invention, the device does not require any external power source such as voltage-generating unit for applying voltage between the electrodes. The device requires at least one detector selected from a group comprising voltmeter, ammeter, current integrator, and a combination thereof, wherein combination thereof is not limited. A conductor with high current collection effect, such as carbon and metal, may be used as the material of each of the working and counter electrodes so that cell reaction can rapidly proceed in the measurement of electrical quantity, etc. The carbon may be any commercial carbon such as carbon felt, and the metal may be any metal with high conductivity such as gold, platinum, silver, lead, etc.

The device of the present invention can be used for the quantitative determination of a sample substance on the basis of the electrical energy generated in the reaction of an electroactive substance in the working electrode with an electroactive substance in the counter electrode. In measurement, the device of the present invention receives as cell current the electrical energy generated in reaction of an electroactive substance in the working electrode and an electroactive substance in the counter electrode, wherein the amount of the sample substance can be derived from the cell current. A wide variety of electroactive components and chemical species can be analyzed by selection of a suitable electroactive substance introduced into the electrodes.

Each electrochemically active substance (electrochemically active species) in solution form exhibits an electrode potential inherent in the substance itself. The electrochemically active substances producing a potential difference between electrodes can be electrolyzed by applying sufficient potential difference. In this case, an oxidation reaction occurs in one electrode, and a reduction reaction occurs in another electrode. This is the principle of electrolysis where electrical energy is converted into chemical energy.

Generally speaking, an electric potential occurring in electrode oxidation is often higher than an electric potential in electrode reduction, so that electrolysis does not proceed (i.e., coulometric analysis cannot be performed) in the absence of a certain electric potential, such as potential difference applied by an external power source.

According to the present invention, however, chemical energy can be converted into electrical energy spontaneously and rapidly in the absence of potential difference applied by an external power source. Conversion of chemical energy into electrical energy can be achieved by constructing the galvanic cell such that ions can pass through a substance which separates the counter electrode and the working electrode. The counter electrode is impregnated with a substance reduced at an extremely high potential, such as hexacyanoferrate (III) ion and/or permanganate ion as electroactive substance, and the working electrode is impregnated with a substance undergoing oxidization at an extremely low potential, such as reduced 5-methylphenazinium methyl sulfate, reduced 1-methoxy-5-methylphenazinium methyl sulfate, reduced 9-dimethylaminobenzo [α] phenoxazine-7-ium chloride, reduced 3,7-bis(dimethylamino)phenothiazine-5-ium chloride, hexacyanoferrate (II) ion or ascorbic acid. That is, the quantity of the sample substance can be quantitatively determined by measuring the electrical energy generated by cell reaction as converted from the chemical energy possessed by the sample substance.

For example, no reaction occurs between a working electrode containing phenazine methosulfate as a mediator and a counter electrode containing potassium hexacyanoferrate (III) as an electroactive substance because the electroactive substance and the mediator both are in oxidized form. If a reducing substance, such as NADH or a derivative thereof, is added to the working electrode, then the phenazine methosulfate is reduced. The potential of reduced phenazine methosulfate is lower than that of hexacyanoferrate (III) ion. This generates a potential difference depending on an electrochemical potential between the working and counter electrodes. As a result, cell reaction occurs and this reaction continues until reduced phenazine sulfate is completely oxidized if a sufficient amount of hexacyanoferrate (III) ion is present in the counter electrode. The current flowing during the cell reaction is measured for the quantitative determination of the reducing agent which contains reduced phenazine methosulfate. That is, NADH and its derivative can be quantitatively determined.

In addition, the present method for the quantitative determination of a substance comprises quantitatively determining a substance as a substrate of quinone-dependent dehydrogenase. Quantitative determination involves injecting a sample containing quinol resulting from reaction of quinone-dependent dehydrogenase with the substrate in the presence of quinone into the working electrode in a galvanic cell, wherein the working electrode and the counter electrode are separated by a substance permitting ions to pass therethrough. The counter electrode is impregnated with an electroactive substance, so that the voltage, current, or electrical quantity generated between the electrodes is measured without applying voltage from an external power source.

The quinol used may be an ubiquinol derivative ($CoQ_nH_2$) represented by the following formula [I], wherein n is the number of repeating units of isoprene residue. Particularly preferred are one or more ubiquinol derivatives selected from the group consisting of $CoQ_0H_2$, $CoQ_1H_2$ and $CoQ_2H_2$.

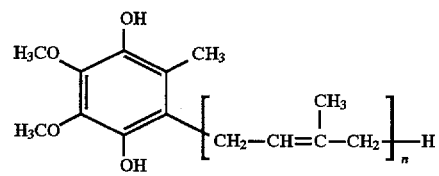

(n is an integer of 0 to 10)

The quinol used is usually a benzoquinone or ubiquinone derivative. In particular, ubiquinones having no side chain (e.g. isoprene residue) such as $CoQ_0$(2,3-dimethoxy-5-methyl-1,4-benzoquinone) or having 1 or 2 short side chains (i.e., n is 0, 1 or 2 in the following formula [II]) such as $CoQ_1$ and $CoQ_2$ are preferably used because of their water-solubility, ease of handling, ease of occurrence of a self-driving discharge reaction, as well as ease of occurrence of a self-driving discharge reaction with hexacyanoferrate (III) ions, i.e., a typical electroactive substance in the working electrode. $CoQ_0$ is particularly preferred because it is inexpensive and effective as the electron acceptor for quinon-dependent dehydrogenase.

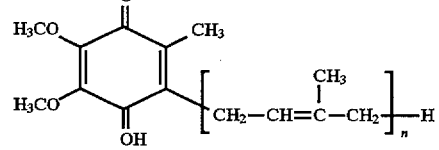

(n is an integer of 0 to 10)

The quantitative determination of a sample is feasible within a short period of time (for example, approximately 30 seconds) for concentrations no higher than 25 mM. The quantitative determination of a sample is also feasible for concentrations greater than 25 mM although it requires a longer period of time.

The quinone-dependent dehydrogenase referred to in the present invention is a group of dehydrogenases which can utilize quinone as a receptor of electrons occurring on the oxidation of a substance as the substrate of the enzyme. Examples of such enzymes are alcohol dehydrogenase (EC 1. 1. 99. 8), glucose dehydrogenase [J. Biotechnology, 18 (1991) 103], aldehyde dehydrogenase [Methods in Enzymology, vol. 89 (1982), 141–145], amine dehydrogenase ("Principles and Applications of Quinoproteins", Marcel Dekker, Inc. 73–95 (1993); Biochem. J. (1983) 211, 535–541), AND(P)H-quinone oxidoreductase (EC 1. 6. 99. 2), etc.

Hence, the quinone-dependent dehydrogenase used may be alcohol dehydrogenase with ethanol as substrate, fructose dehydrogenase with fructose as substrate, aldose dehydrogenase with aldose as substrate, aldehyde dehydrogenase with aldehyde as substrate, glycerol dehydrogenase with glycerol as substrate, sorbitol dehydrogenase with sorbitol as substrate, amine dehydrogenase with amines as substrate, and NAD(P)H-quinone oxidoreductase with NADH or NADPH as substrate.

A combination of quinone-dependent glucose dehydrogenase and quinone-dependent fructose dehydrogenase in the presence of invertase enables the determination of the total amount of sucrose, glucose and fructose as their substrates.

To improve analysis sensitivity, a fixing screw with collar, is used to press the working electrode to secure adhesion between the working electrode and a substance separating the working electrode and the counter electrode.

The electroactive substance is supplied to the counter electrode through a liquid-supplement hole provided on the bottom of the galvanic cell. The role of a rubber cap provided on the top of the galvanic cell is to prevent drying of the electrodes.

Figure 1B:
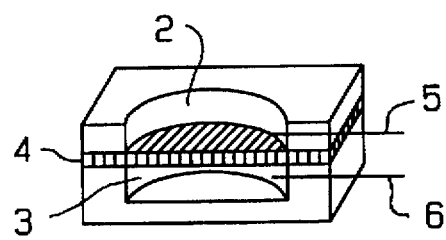

FIG. 1 is a schematic drawing of a device used in the present invention. Galvanic cell 1 includes working electrode 2, counter electrode 3, and an ion-exchange membrane serving as separating membrane 4 (cation exchange membrane CMV produced by Asahi Glass Co., Ltd.). The cell is joined via current collection wires 5 and 6 to electroanalyzer 40 (NDCM-1 manufactured by Nichino Keiki Co., Ltd.). Prescribed electrolyte is introduced into the working and counter electrodes 2 and 3, and a certain amount of a sample solution is injected by a syringe into the working electrode 2. The sample can be quantitatively determined by measuring electrical quantity flowing in cell reaction occurring according to the aforementioned principle.

EXAMPLES

Hereinafter, the present invention is described in more detail with reference to Examples, which are not intended to limit the scope of the present invention.

[Example 1]

Selection of Mediator

The amount of time required for quantitative measurement of NADH using various mediators were determined using the device as shown in FIG. 1. Measurement time is the amount of time required for completion of 95% of the reaction.

The mediators used in the working electrode were potassium hexacyanoferrate (III), Vitamin $K_3$, methylene blue, phenazine methosulfate (all available from Wako Junyaku Kogyo Co., Ltd. ), methoxyphenazine methosulfate (available from Dojin Kagaku Kenkyusho), and Meldola blue (available from Nakarai Tesuku Co., Ltd. ). 3 ml of 0.1M mediator in 0.1M phosphate buffer, pH 7.0, was used as an electrode solution. Sample substance NADH ($10^{-3}$M) was quantitatively determined using the device of FIG. 1 wherein the counter electrode contained 0.1M potassium hexacyanoferrate (III) (dissolved in 3 ml of 0.1M phosphate buffer, pH 7.0) as an electrode solution and no external power source applying a voltage to the device.

As shown by the results in Table 1, the measurements could be obtained in a very short time (about 30 seconds) with phenazine methosulfate, methoxyphenazine methosulfate, and Meldola blue as mediator.

TABLE 1

| mediator | measurement time (seconds) |
| --- | --- |
| Vitamin $K_3$ | measurement not possible |
| potassium hexacyanoferrate (III) | 900 |
| methylene blue | 180 |
| phenazine methosulfate | 30 |
| methoxyphenazine methosulfate | 33 |
| Meldola blue | 31 |

[Example 2]

Measurement of NADH

NADH was measured with the electroanalyzer of Example 14 including the galvanic cell of Example 13.

Figure 2:
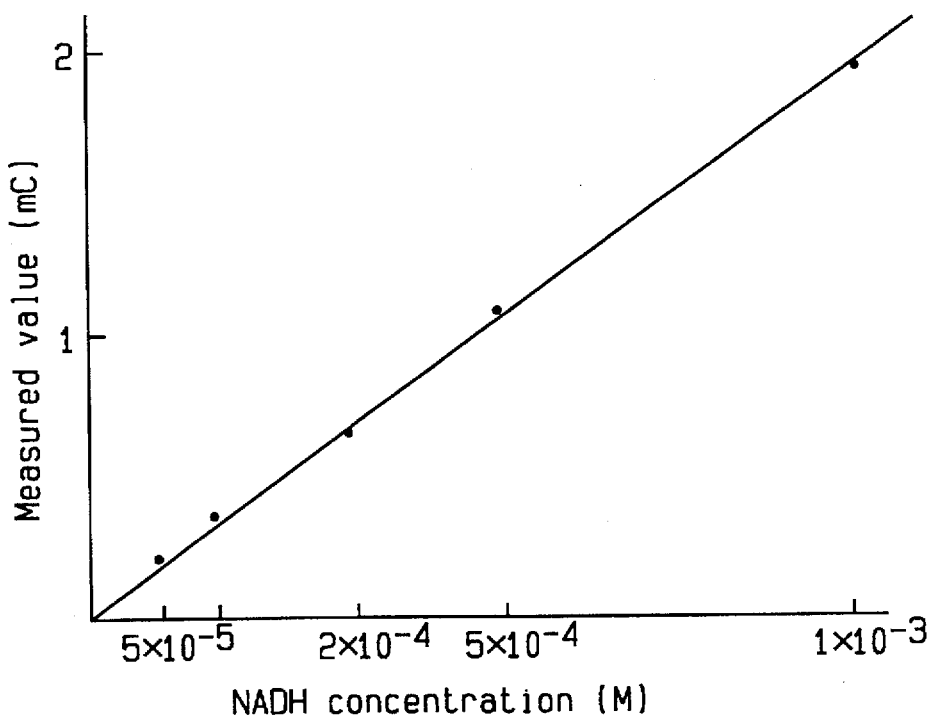
FIG. 2 is a graph showing the relationship between NADH concentration and measured values.

In the galvanic cell, upper felt 9 and lower felt 10 were both composed of carbon felts with a top surface area of 7 $cm^2$, thickness of 5 mm, and volume of 3.5 $cm^3$ (GF-20-5F produced by Nippon Carbon Co., Ltd.), and separating membrane 4 was an ion-exchange membrane (cation exchange membrane CMV produced by Asahi Glass Co., Ltd.). For quantitative determination of NADH (10 μl ) (dissolved at predetermined concentrations in 40 mM phosphate buffer, pH 7.0), the working electrode was impregnated with 3 ml of 0.1M phenazine methosulfate and the counter electrode was impregnated with 3 ml of 0.1M potassium hexacyanoferrate (III) (each dissolved in 0.1M phosphate buffer, pH 7.0). As shown in FIG. 2, the measurement results obtained in the present coulometric method are in a good linear relationship with the actual concentrations of NADH.

Reproducibility was excellent with 2% coefficient of variation (hereinafter referred to as "CV") on 10 repeated measurements. When additional measurements were carried out in the same way using the galvanic cell with a carbon felt (GF-20-5F produced by Nippon Carbon Co., Ltd.) as the hydrophilic and conductive material of the working and counter electrodes, the results were also in a good linear relationship with the actual concentrations of NADH. In addition, stable measurements of 10 μl of $5 \times 10^{-4}$M NADH were obtained within a 2% CV on 200 repeated runs or more.

[Example 3]

Measurement of qlutamic acid by quantitative determination of NADH formed by glutamate dehydrogenase Using the present invention, glutamic acid was quantitatively determined with glutamate dehydrogenase which has excellent substrate specificity and stability as discovered by the present inventors (Japanese Patent unexamined Publication No. 38744/94). This enzyme catalyzes the following reaction:

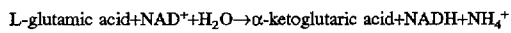

L-glutamic acid+NAD$^+$+H$_2$O→α-ketoglutaric acid+NADH+NH$_4^+$

That is, 10 μl of glutamate dehydrogenase (4 U/ml 20 mM phosphate buffer, pH 7.0), as described in Example 1 of Japanese Patent Application No. 194,245/92, was mixed at 30° C. for 3 minutes with 990 μl sodium glutamate solution at a predetermined concentration containing NAD+(20 mg/ml) as substrate (20 mM phosphate buffer, pH 7.0), and the mixture was measured in the same conditions as in Example 2.

Figure 3:
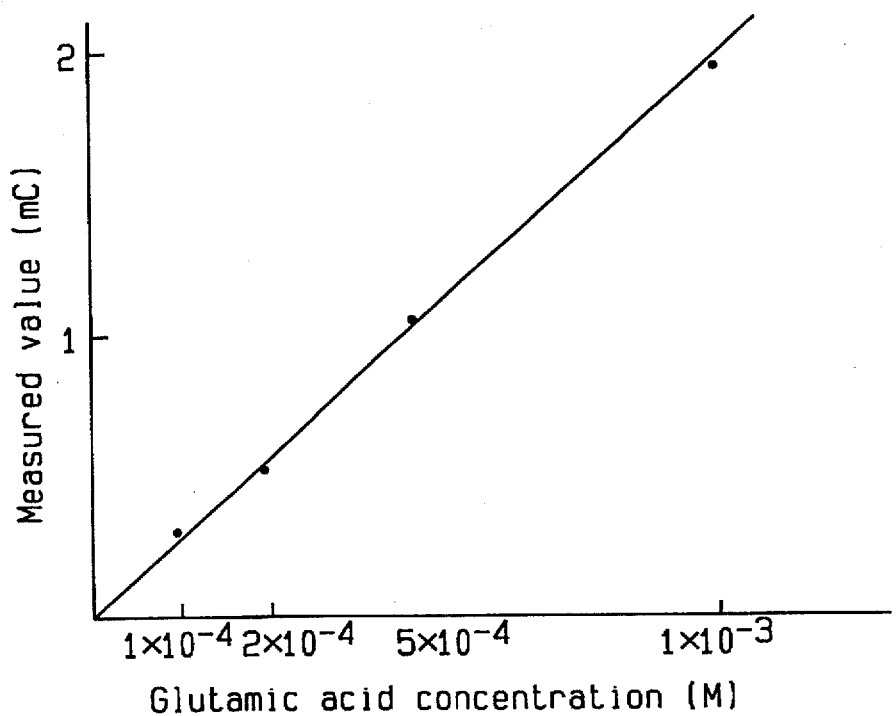
FIG. 3 is a graph showing the relationship between glutamic acid concentrations and measured values.

As shown in FIG. 3, there is a good linear relationship between the values obtained with NADH as an indicator and the actual concentrations of glutamic acid. The glutamic acid content of a sample of commercial soy sauce was determined in the same manner. The 11.2 g/l glutamic acid content thusly determined was in good agreement with 11.3 g/l glutamic acid content as determined with an amino acid analyzer (JLC-300 manufactured by Nihon Denshi Co., Ltd.) The content as determined for the same sample by glutamic acid assay kit (manufactured by BMY Co., Ltd.) was 11.0 g/l. In the present invention, the measurements could be obtained relatively quickly, i.e., within approximately 50 seconds (or approximately 4 minutes including the enzyme reaction time), whereas using the amino acid analyzer and glutamic acid assay kit, the measurements were obtained in approximately 1.5 hours and 20 minutes, respectively.

According to a conventional manner, the enzyme used in this example could be immobilized on the electrode for use.

[Example 4]

Measurement of qlutamic acid by quantitative determination of NADH derivative formed by glutamate dehydrogenase Glutamic acid was determined in a similar manner as in Example 3 wherein enzyme reaction was carried at 50° C. for 20 minutes in the presence of 3-acetylpyridine NAD (produced by Sigma Co. Ltd.) as coenzyme for glutamate dehydrogenase (i.e., 3-acetylpyridine NADH formed by enzyme reaction was used as an indicator). The results had a good linear relationship with the actual concentrations of glutamic acid. The measurements could also be obtained within a relatively short time (about 30 seconds).

[Example 5]

Chemical oxygen demand (COD) measurement (1)

Various samples were measured for COD using the device of FIG. 1 wherein the working electrode was impregnated with 3 ml of 1N hydrochloric acid containing 0.1M calcium chloride as an electrode solution and wherein the counter electrode was impregnated with 3 ml of 1N hydrochloric acid containing 0.01M potassium hexacyanoferrate (II) (ion electroactive substance) and 0.1M potassium chloride as an electrode solution.

Samples consisted of two kinds of waste water (A and B) from a factory and two kinds of treatment sewage (C and D), wherein A, B, C, and D were collected from Handa City, Aichi Prefecture, Japan, and 1 mg 0/l and 10 mg 0/l glucose standard solutions (described in Japanese Industrial Standards No. JIS K8824).

Measurements were carried out as follows:

2 ml sample, 0.4 ml of 47% sulfuric acid, and 0.2 ml of 0.025N potassium permanganate were introduced in this order into a 10 ml test tube with a cap. The tube was sealed, heated for 5 minutes, and cooled to room temperature. Subsequently, 10 μl of the sample was injected with a syringe into the working electrode of the above device. Separately, the same sample was also measured according to the method as described in Japanese Industrial Standard No. JIS K0102.

As can be seen from the results in Table 2, the measured values according to the present method are in good agreement with those of the JIS K0102 method. In the present method, the measurements could be obtained in a short period of time (about 30 seconds) with a trace amount of sample.

Similar results could be obtained with the above device under similar conditions using galvanic cell having a carbon felt (GF-20-5F produced by Nippon Carbon Co., Ltd.) as the hydrophilic and conductive materials of the working and counter electrodes.

TABLE 2

Result of COD measurement

| sample | present method | JIS K0102 method |
|---|---|---|
| factory waste water A | 8.3 | 7.8 |
| factory waste water B | 8.0 | 7.6 |
| treatment sewage C | 11.0 | 11.5 |
| treatment sewage D | 8.1 | 9.0 |
| glucose standard solutions | | |
| 1 mg 0/l | 1.1 | 1.2 |
| 10 mg 0/l | 9.8 | 10.5 | unit: mg 0/l

[Example 6]

Chemical oxygen demand (COD) measurement (2)

Various samples were measured for COD with the device of FIG. 1 having the working electrode impregnated with 3 ml of 1.5N sulfuric acid as an electrode solution and having the counter electrode impregnated with 3 ml of 1.2N sulfuric acid containing 0.02M potassium hexacyanoferrate (II) and 0.02M potassium hexacyanoferrate (III) (ion electroactive substance) as an electrode solution. Samples consisted of two kinds of effluent (A and B) from septic tanks and two kinds of waste water (C and D) from an office, wherein A, B, C, and D were collected from Urawa City, Saitama Prefecture, Japan, and 1 mg 0/l and 10 mg 0/l glucose standard solutions (described in JIS K8824).

Measurements were carried out as follows:

2 ml sample, 0.4 ml of 47% sulfuric acid, and 0.2 ml of 1M silver nitrate, 0.2 ml of 0.025N potassium permanganate were introduced in this order into a 10 ml test tube with a cap. The tube was sealed, heated for 5 minutes, and cooled with water to room temperature. Subsequently, 10 μl of the sample thusly treated was injected with a syringe into the working electrode of the device. Separately, the same sample was also measured according to the method as described in JIS K0102.

As shown by the results in Table 3, the measured values according to the present method are in good agreement with those obtained by the JIS K0102 method. In the present method, the measurements could be obtained in a short period of time (about 30 seconds) with a trace amount of sample.

Similar results could be obtained under the same conditions with the galvanic cell having a carbon felt (GF-20-5F produced by Nippon Carbon Co., Ltd.) as the hydrophilic and conductive material of the working and counter electrodes.

TABLE 3

Result of COD measurement

| sample | present method | JIS K0102 method |
|---|---|---|
| septic tank effluent A | 11.0 | 12.0 |
| septic tank effluent B | 6.7 | 7.4 |
| office waste water C | 23.5 | 24.0 |
| office waste water D | 21.0 | 20.9 |
| glucose standard solutions | | |
| 1 mg O/l | 1.1 | 1.2 |
| 10 mg O/l | 9.8 | 10.5 | unit: mg O/l

[Example 7]

Measurement of ascorbic acid

Ascorbic acid solutions (1–200 mg/100 ml) were measured with the device of FIG. 1 having the working electrode impregnated with 3 ml of 10 mM methylene blue (dissolved in 0.4M phosphate buffer, pH 5.0) and having the counter electrode impregnated with 3 ml of 0.4M potassium hexacyanoferrate (III) (0.4M phosphate buffer, pH 7.3) as electrode solution. The ascorbic acid contents determined had a good linear relationship to the actual ascorbic acid contents. The measurements could be obtained in a short period of time (about 40 seconds) with a trace sample amount of 5 µl. Stable results were obtained within a 2% CV on repeated measurements of the same sample.

Similar results can be obtained with the above device under similar conditions using 0.4M phosphate buffer, pH 5.0, as an electrode solution in the working electrode, or the use of galvanic cell having a carbon felt (GF-20-5F produced by Nippon Carbon Co., Ltd.) as the hydrophilic and conductive materials of the working and counter electrodes.

[Example 8]

Measurement of ascorbic acid in various commercial foods

The contents of ascorbic acid in various commercial foods were determined using the device of FIG. 1 with the working electrode impregnated with 3 ml of 0.4M phosphate buffer, pH 5.0, as an electrode solution and with the counter electrode impregnated with 3 ml of 0.1M potassium hexacyanoferrate (III) (0.4M phosphate buffer, pH 7.3) as an electrode solution. Separately, the same samples were also measured by titration with indophenol and high performance liquid chromatography (HPLC) (Standard Methods of Analysis in Food Safety Regulation published by Shadanhojin Nippon Shokuhin Eisei Kyokai (Japan Food Hygiene Association, foundation), the 1989 edition, pp. 361–363). Table 4 shows good agreement among the results.

TABLE 4

Comparison of measured ascorbic acid contents

| sample | indophenol titration method | HPLC method | the present method |
|---|---|---|---|
| 100% orange juice | 27.6 | 28.9 | 28.6 |
| 10% orange juice | 29.7 | 33.1 | 32.0 |
| non alcoholic beverage | 5.1 | 7.3 | 5.8 |
| cabbage | 29.1 | 33.2 | 28.1 |
| powdered milk | 43.4 | 48.8 | 46.4 | unit: mg/100 mg

[Example 9]

Measurement of ethanol by quantitative determination of $CoQ_oM_2$ formed by alcohol dehydrogenase According to the present method, ethanol was measured using the device of FIG. 1 with the working electrode impregnated with 0.4M phosphate buffer, pH 5.0, as an electrode solution and with the counter electrode impregnated with 0.45M potassium hexacyanoferrate (III) (0.4M phosphate buffer, pH 7.3) as an electrode solution in the presence of the alcohol dehydrogenase which was discovered by the present inventors to have excellent substrate specificity and stability (Japanese Patent Publications No. 12278/88).

The enzymatic reaction used in this example is as follows:

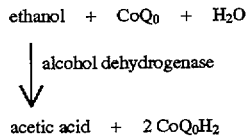

That is, 5 µl of 100 U/ml alcohol dehydrogenase (5 mM phosphate buffer, pH 6.0, 0.1% Triton X-100) was mixed with 50 µl of 250 mM $CoQ_0$ and 445 µl ethanol solution at a predetermined concentration (½ Macwillvein buffer, pH 5.0) as substrate and allowed to stand for 15 min. at room temperature. Then, 5 µl solution was injected into the working electrode of the device shown in FIG. 1, and the electrical quantity was determined with a current integrating meter.

Figure 4:
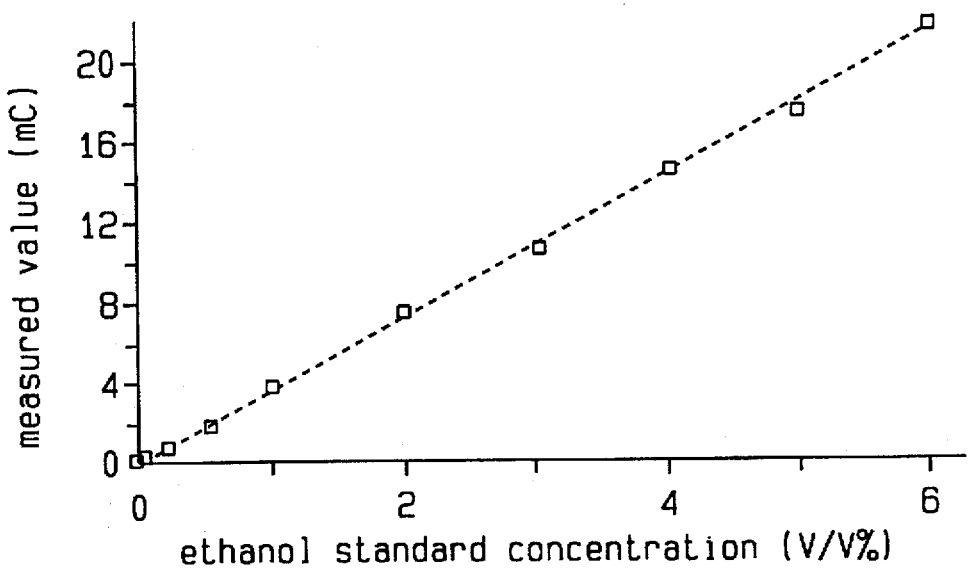
FIG. 4 is a graph showing the relationship between ethanol concentrations and measured values.

FIG. 4 shows the measurement results. As seen from FIG. 4, there is a good linear relationship between the ethanol concentration and the electrical quantity determined with a current integrating meter. Stable results were obtained within a 2% CV on 10 repeated measurements of the same sample.

In the same manner as described above, the ethanol contents in various commercial foods were determined.

For comparison, the same sample was further analyzed by gas chromatography [GC-6A gas chromatograph (with a flame ionization detector) manufactured by Shimadzu Corporation, column size: 2 mm (inner diameter)*2 m, packed material: Chromosorb 101, mesh: 80/100, column temperature: 160° C., carrier gas: 40 ml/min. nitrogen].

As shown in Table 5, the results are in good agreement with those of the present invention.

TABLE 5

Comparison of ethanol measurements

| sample/method | present method (V/V %) | gas chromatography (V/V %) |
|---|---|---|
| soy source | 2.72 | 2.78 |
| sweet sake seasoning | 0.74 | 0.74 |
| vinegar | 0.23 | 0.23 |
| beer | 4.41 | 4.31 |
| sake | 15.29 | 15.76 |
| distilled spirits | 20.80 | 20.82 |
| red wine | 12.14 | 11.95 |
| white wine | 12.15 | 11.70 |
| miso (bean paste) | 1.35 | 1.36 |

TABLE 6

Comparison of glucose measurements

| sample/Method | present method (W/V %) | HPLC (W/V %) | enzyme kit W/V % |
|---|---|---|---|
| beverage drink | 6.10 | 6.10 | 6.68 |
| apple juice | 4.40 | 4.55 | 4.84 |
| vinegar | 1.15 | 1.20 | 1.13 |
| mixed vinegar | 13.21 | 14.37 | 14.16 |
| marinade | 9.48 | 9.86 | 9.33 |
| sauce | 8.02 | 8.76 | 8.64 |

[Example 10]

Measurement of glucose by quantitative determination of $CoQ_0H_2$ formed by glucose dehydrogenase The measurement of glucose according to the present invention was conducted using glucose dehydrogenase prepared from *Gluconobacter suboxydans* IFO 12528 by the method described in J. Biochem. 105, 633–637 (1989).

The enzymatic reaction used in this example is as follows:

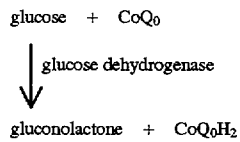

glucose + $CoQ_0$
↓ glucose dehydrogenase
gluconolactone + $CoQ_0H_2$

That is, 5 µl of 60 U/ml glucose dehydrogenase (40 mM phosphate buffer, pH 6.0, 01.% Triton X-100) was mixed with 8 µl of 250 mM $CoQ_0$ and 87 µl glucose solution at a predetermined concentration (50 mM phosphate buffer, pH 6.5) as substrate and allowed to stand for 15 min. at room temperature. 5 µl of the solution was measured under the same conditions as in Example 9.

Figure 5:
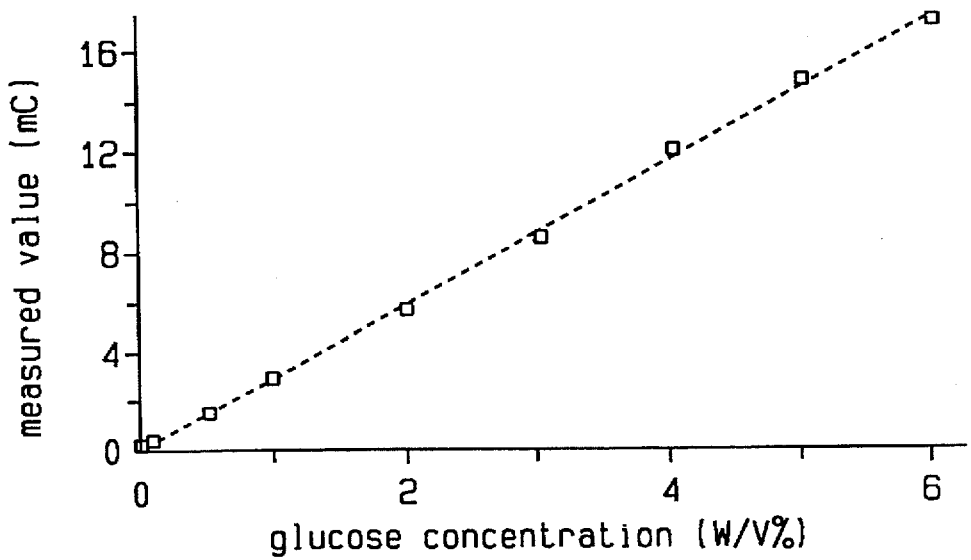
FIG. 5 ia a graph showing the relationship between glucose concentrations and measured values.

FIG. 5 shows the measurement results. There is a good linear relationship between the glucose concentration and the electrical quantity determined with the current integrating meter. Stable results were obtained within a 2.4% CV on 10 repeated measurements of the same sample.

In the same manner as described above, the glucose contents in various commercial foods were determined. For comparison, the same sample was further analyzed by high performance liquid chromatography [Chromatograph LC-6A manufactured by Shimadzu Corporation, detector: Shodex RISE-51 manufactured by Showa Denko K. K., column: Asahi Pak NH2P-50, 4.6 mm I.D. * 250 mm, manufactured by Asahi Chemical Industry Co., Ltd., mobile phase: 70% acetonitrile, flow rate: 0.8 ml/min., column temperature: room temperature, injection volume: µl ] as well as by the enzyme kit method (F-kit product No. 716260 produced by Boehringer Mannheim GMBH).

As shown in Table 6, the results are in good agreement with those of the present invention.

[Example 11]

Measurement of fructose by quantitative determination of $CoQ_0H_2$ formed by fructose dehydrogenase The measurement of fructose according to the present invention was conducted using fructose dehydrogenase prepared from *Gluconobacter industrius* IFO 3260 by the method described in J. Bacteriol. 145, 814–823 (1981).

The enzymatic reaction used in this example is as follows:

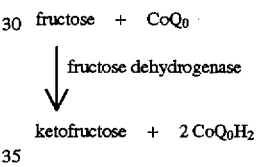

fructose + $CoQ_0$
↓ fructose dehydrogenase
ketofructose + $2 CoQ_0H_2$

That is, 5 µl of 80 U/ml fructose dehydrogenase (50 mM citrate buffer, pH 5.0) was mixed with 8 µl of 250 mM $CoQ_0$ and 87 µl fructose solution at a predetermined concentration (50 mM phosphate buffer, pH 6.5) as substrate and allowed to stand for 15 min. at room temperature. 5 µl of the solution was measured under the same conditions as in Example 9.

Figure 6:
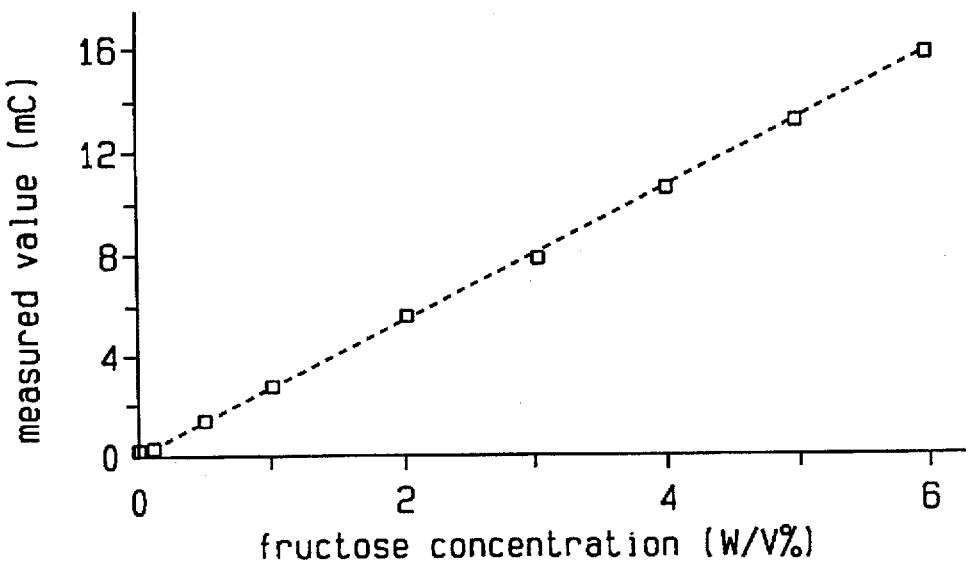
FIG. 6 is a graph showing the relationship between fructose concentrations and measured values.

FIG. 6 shows the measurement results. There is a good linear relationship between the fructose concentration and the electrical quantity determined with a current integrating meter. Stable results were obtained within a 5.0% CV on 10 repeated measurements of the same sample.

In the same manner as described above, the fructose contents in various commercial foods were determined. For comparison, the same sample was further analyzed by high speed liquid chromatography [Chromatograph LC-6A manufactured by Shimadzu Corporation; detector: Shodex RISE-51 manufactured by Showa Denko K. K.; column: Asahi Pak NH2P-50, 4.6 mm (inner diameter) *250 mm, manufactured by Asahi Chemical Industry Co., Ltd.; mobile phase: 70% acetonitrile, flow rate: 0.8 ml/min.; column temperature: room temperature, injection volume: 20 µl] as well as by the enzyme kit method (F-kit product No. 716260 produced by Boehringer Mannheim GMBH).

As shown in Table 7, the results are in good agreement with those of the present invention.

TABLE 7

Comparison of fructose measurements

| sample/method | present method (W/V %) | HPLC (W/V %) | enzyme kit (W/V %) |
|---|---|---|---|
| apple juice | 6.20 | 5.69 | 6.49 |
| orange juice | 7.76 | 7.31 | 7.48 |
| sauce | 17.13 | 15.01 | 16.52 |
| vinegar | 0.72 | 0.66 | 0.71 |
| ketchup | 10.93 | 10.13 | 9.30 |

TABLE 8

Comparison of sugar measurements

| sample/method | present method (W/V %) | somogyi method (W/V %) |
|---|---|---|
| orange juice | 11.34 | 11.61 |
| sake | 2.66 | 2.85 |
| vinegar | 6.45 | 6.57 |
| marinade | 6.39 | 6.38 |
| sauce | 25.77 | 25.55 |

[Example 12]

Measurement of sugar content (total amount of sucrose, glucose and fructose) by quantitative determination of $CoQ_0H_2$ formed by invertase, glucose dehydrogenase and fructose dehydrogenase The measurements of sugar contents according to the present invention were conducted using commercial invertase (β-fructosidase produced by Boehringer Mannheim GMBH), the glucose dehydrogenase in Example 10, and the fructose dehydrogenase in Example 11.

The enzymatic reaction used in this example is as follows:

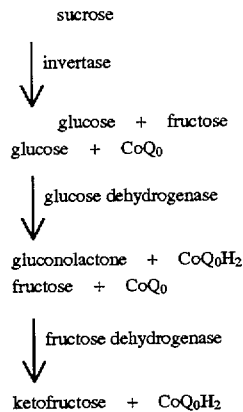

That is, 5 μl of 1200 U/ml invertase, 40 U/ml glucose dehydrogenase, and 40 U/ml fructose dehydrogenase in 50 mM citrate buffer, pH 5.0, were mixed with 8 μl of 250 mM $CoQ_0$ and 87 μl fructose solution at a predetermined concentration (50 mM phosphate buffer, pH 6.5) as substrate and allowed to stand for 15 min. at room temperature. 5 μl of the solution was measured under the same conditions as in Example 9.

Figure 7:
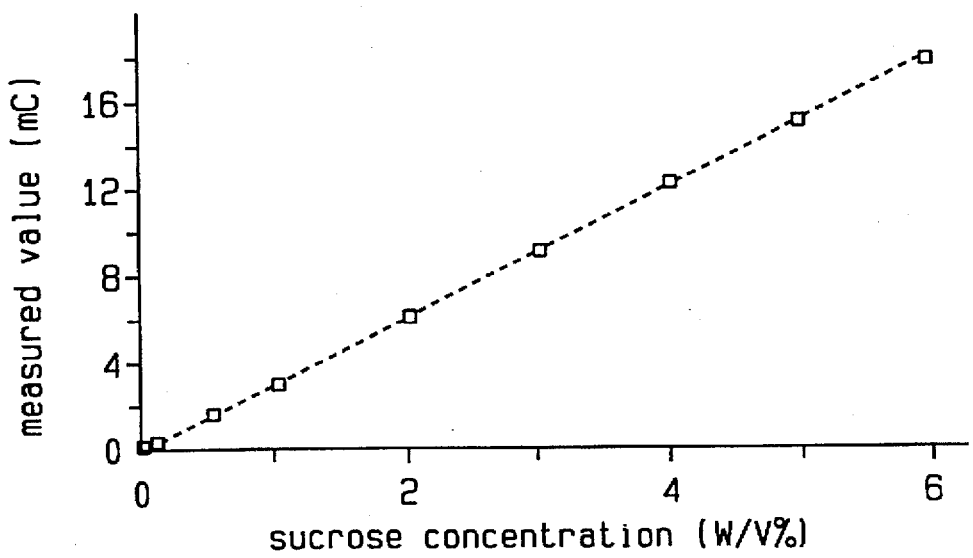
FIG. 7 is a graph showing the relationship between sucrose concentrations and measured values.

FIG. 7 shows the results. There is a good linear relationship between the sugar concentration and the electrical quantity determined with the current integrating meter. Stable results were obtained within a 3.8% CV on 10 repeated measurements of the same sample.

The sugar contents in commercial foods were determined under the same conditions. For comparison, the same sample was further analyzed using the Somogyi method [annotation in the hygienic test method (1990) complied by Pharmaceutical Society of Japan and published by Kanehara Shuppan].

As shown in Table 8, the results are in good agreement with those of the present invention.

[Example 13]

Figure 8:
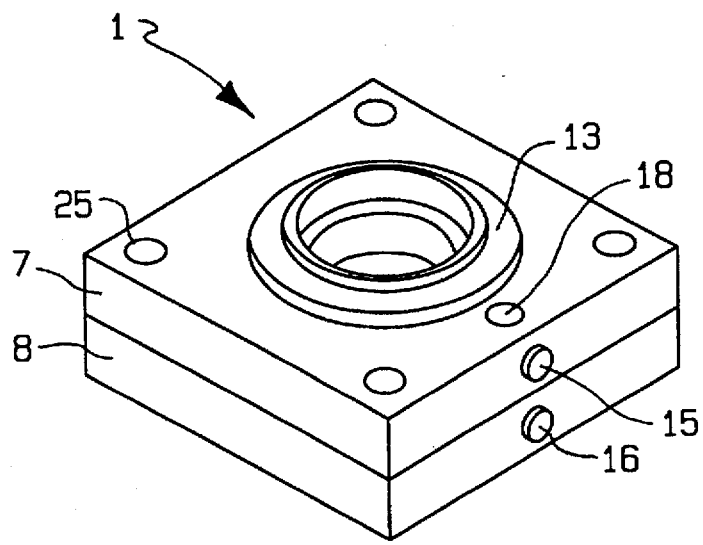
FIG. 8 is a perspective view of the galvanic cell in the present examples.
Figure 9:
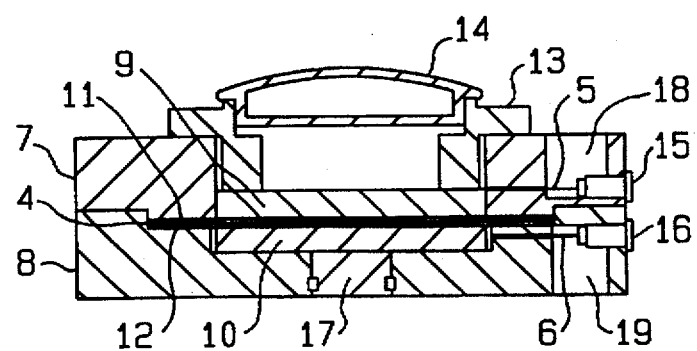
FIG. 9 is a cross-sectional view of the galvanic cell shown in FIG. 8.
Figure 10:
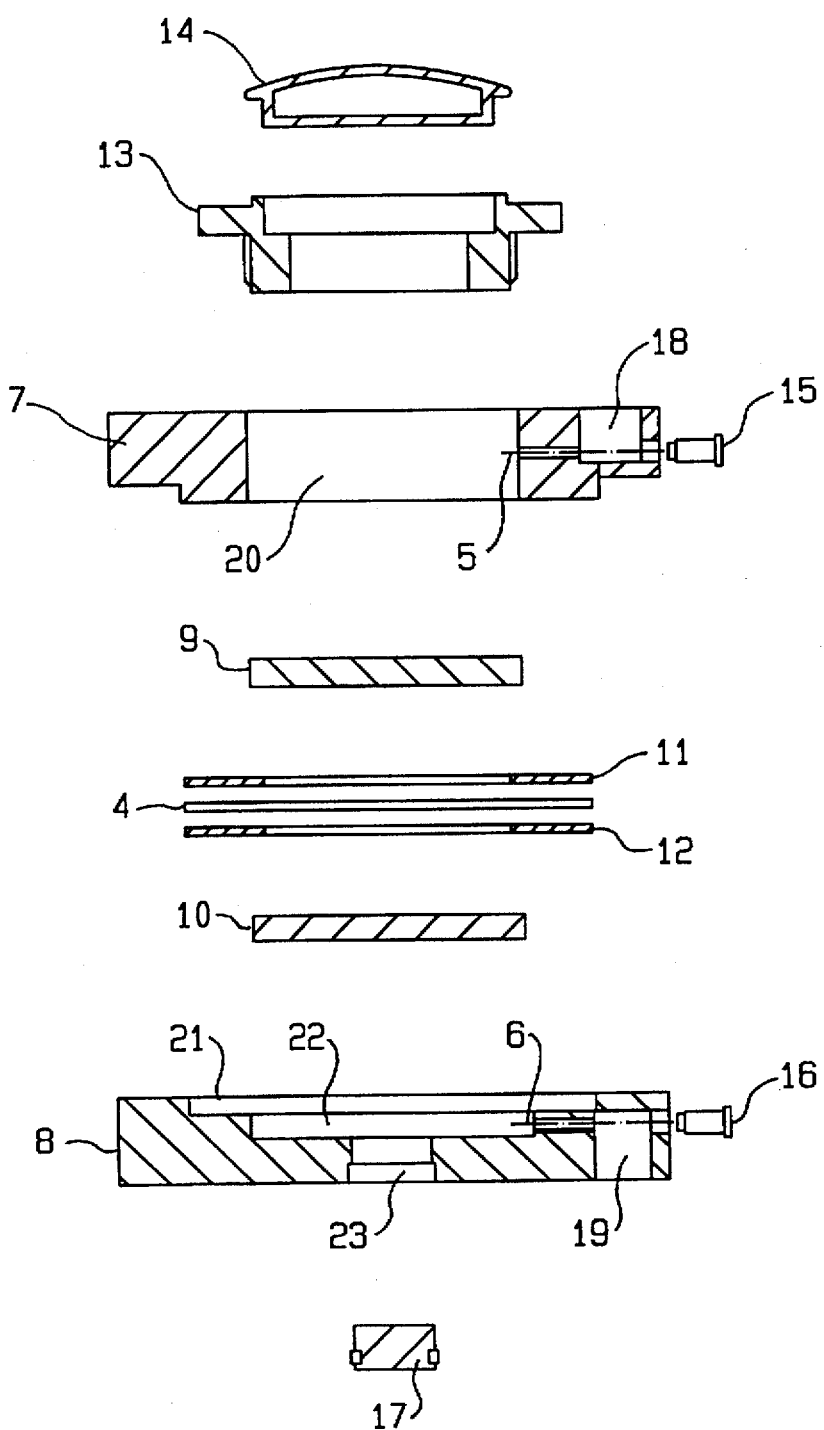
FIG. 10 is a cross-sectional view of the structure of the galvanic cell shown in FIG. 8.

The galvanic cell according to the present invention is described by reference to the drawings. FIG. 8 is a perspective view of the galvanic cell (without cap 14); FIG. 9 is a cross-sectional view; and FIG. 10 is a cross-sectional view of the structure of the galvanic cell.

In this example, the galvanic cell includes upper component 7 and lower component 8 each made of an electrical insulating material such as plastics, upper felt 9 and lower felt 10, separating membrane 4, packings 11 and 12 made of a silicone resin, etc., collar-head component 13, electrode terminals 15 and 16 to which current collection electrode wires 5 and 6 are connected, bottom lid 17, and cap 14.

Separating membrane 4 is an ion-permeable separating membrane such as glass filter, salt bridge, ion-exchange membrane, etc., wherein separating membrane 4 is preferably an ion-exchange membrane such as a cation exchange membrane in order for stable measurements.

Upper felt 9 may be any material being hydrophilic and with excellent conductivity such as carbon felt, preferably with a diameter of 30±10 mm or thereabout and thickness of 2–6 mm as will be described below. The lower felt 10 may be any hydrophilic and conductive material, and it preferably has the same size and thickness as the upper felt 9 so that felts 9 and 10 have low electrical resistance, with the same area in contact with the separating membrane 4.

With respect to current collection wires 5 and 6, platinum or gold is used for preventing occurrence of corrosion responsible for increase in electrical resistance. Electrode terminals 15 and 16 are coated with gold for low electrical resistance so that sufficient conduction is obtainable when terminals come into contact with contact points of the measurement device.

Upper component 7, provided vertically with penetrating hole 20, has a bottom with a convex-shaped step fitting a concave part of lower component 8. Upper component 7 is also provided horizontally with a thin hole extending from the side to penetrating hole 20, said thin hole containing current collection electrode wire 5 joined with solder to electrode terminal 15. A part of the thin hole crosses sealing hole 18 extending vertically from the top face to below the thin hole. After insertion of current collection electrode wire 5 into the thin hole, a resin is introduced into sealing hole 18 so as to fix the electrode and fill in the thin hole, thus preventing the solution in the electrode cell from leaking out through the thin hole.

Lower component 8 is provided with two concave-shaped steps 21 and 22 on the top surface and with liquid-supplement hole 23 in the bottom. Lower component 8 is also provided horizontally with a thin hole extending from the side to concave step 22, said thin hole containing current collection electrode wire 6 joined with solder to electrode terminal 16. Lower component 8 is provided with sealing hole 19 in the same manner as with upper component 7. After insertion of current collection electrode wire 6 into the thin hole, a resin is introduced into sealing hole 19 so as to fix the electrode and fill in the thin hole, thus preventing the solution in the electrode cell from leaking out through the thin hole. Bottom lid 17 equipped with an O-ring is attached detachably to liquid-supplement hole 23.

The galvanic cell is constructed as follows: Lower felt 10 is inserted into deep concave step 22 of lower component 8. Then, round separating membrane 4 with its periphery sandwiched between packings 11 and 12 for preventing mixing anode and cathode solutions is placed on lower felt 10 such that packing 12 is located on hollow concave step 21. Upper component 7 including upper felt 9 inserted into penetrating hole 20 is placed on packing 11 so that convex-shaped step of upper felt 7 fits concave step 21 of lower component 8. In this state, upper component 7 is fixed into lower component 8 with a suitable fixing means such as screw 25, etc. Then, fixing screw with collar 13, is fixed into penetrating hole 20 of upper component 7 so as to allow current collection electrode 5 to be in secure contact with upper felt 9, while upper felt 9 is pressed downward so as to come in close contact with separating membrane 4.

In the galvanic cell according to this embodiment, upper felt 9 serves as the working electrode, and lower felt 10 serves as the counter electrode, and a wide variety of components can be analyzed by selection of a suitable electroactive substance to be introduced into the electrodes.

That is, a sample can be quantitatively determined on the basis of the electrical energy generated from an electroactive sample substance or an electroactive substance produced by reaction of an electroactive sample substance with a mediator in one electrode. The role of the electrode terminals of the galvanic cell is to receive current generated by cell reaction. Therefore, the galvanic cell of the present invention does not require any external power supply for application of voltage or current.

Since a sample introduced into the working electrode is converted into a substance inert to cell reaction when analysis is complete, a plurality of samples can be successively analyzed by injection of a new sample into the working electrode of the galvanic cell. The electroactive substance consumed by cell reaction is supplied as necessary. With bottom lid 17 detached, an electroactive substance is supplied through liquid-supplement hole 23 into the counter electrode. Liquid-supplement hole 23 is preferably 10 mm or more in diameter so that an electroactive substance can be easily introduced.

The role of rubber cap 14 provided on the top of the galvanic cell is to prevent the electrodes from being dried during analysis or in storage.

Fixing screw with collar 13 ensures adhesion between the felt and the separating membrane, thus improving analysis sensibility. For example, if NADH is measured in the absence of fixing screw with collar 13 under the same conditions as in Example 2, the obtained value is lowered (only 60% of theoretical value), and measurements lack accuracy because of poor reproducibility with at least 10% CV.

[Example 14]

Figure 11:
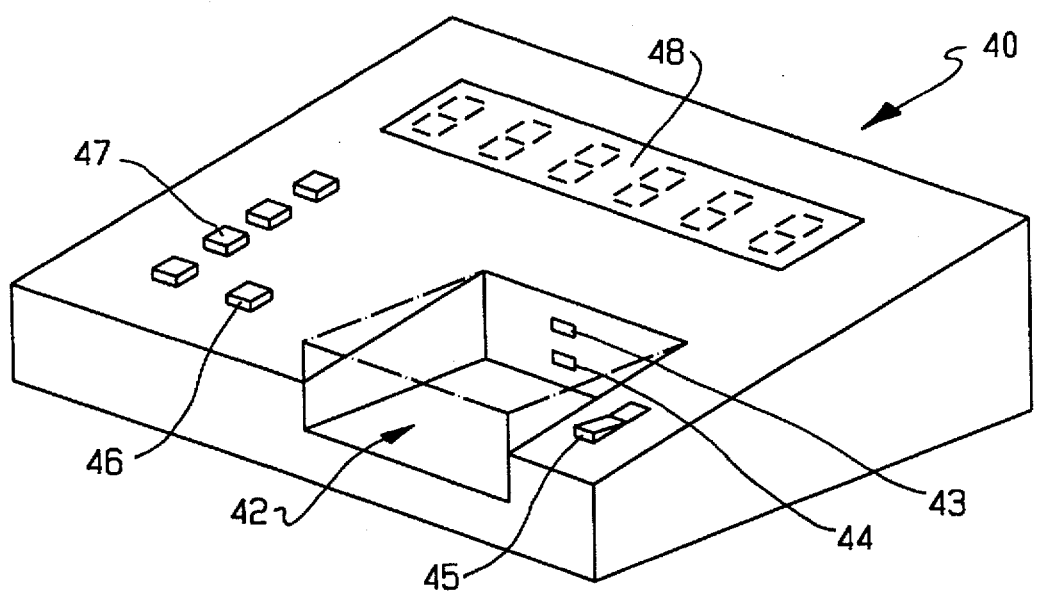
FIG. 11 is a perspective view of the electroanalyzer in the present examples.

The electroanalyzer of the present invention is described by reference to FIG. 11.

Coulometer 40 according to the present invention is provided with cutout part 42 equipped with terminals 43 and 44, electric power switch 45, start button 46, selection button 47 and indication part 48. When galvanic cell 1 illustrated in Example 13 by reference to FIGS. 8–10 is attached as shown in the broken line, electrode terminals 15 and 16 of the galvanic cell 1 come into contact respectively with terminals 43 and 44 of the analyzer, and in this condition, the galvanic cell is ready for measurement. A coulometer (electrical quantity integrator) and a microprocessor are incorporated into the analyzer.

For analysis, the galvanic cell containing a specific electroactive substance is attached to cutout part 42, then the substance to be measured is selected with selection button 47, and start button 46 is pushed, and the sample is injected into the galvanic cell. The role of selection button 47 is to select a conversion formula of deriving the amount of the object substance from electric quantity integrated in the coulometer, and the role of the start button is to clear an internal memory (previously measured value).

According to the analyzer of the present invention, galvanic cell 1 can be easily detached from the main body of analyzer 40, and a sample can be analyzed immediately (without any warm-up time) after the galvanic cell is attached to analyzer 40 which is connected to an electric source. Hence, a plurality of previously prepared galvanic cells can be used for successive automatic multicomponent analysis wherein a cell is exchanged for another cell for each successive measurement.

[Example 15]

Measurements were made under the same conditions as in Example 2, using the galvanic cell including lower felt 10 with a top surface of 7 cm$^3$, thickness of 5 mm, and volume of 3.5 cm$^3$ on the side of the working electrode and upper felt 9 with a varying top surface of 2 to 12 cm$^2$ and a varying volume of 1 to 6 cm$^3$ on the side of the counter electrode. The results are shown in Table 9.

TABLE 9

| felt | A | B | C | D | E |
|---|---|---|---|---|---|
| top surface area of felt (cm$^2$) | 2 | 4 | 7 | 10 | 12 |
| felt thickness (mm) | 5 | 5 | 5 | 5 | 5 |
| volume (cm$^3$) | 1 | 2 | 3.5 | 5.0 | 6 |
| number of times of feasible measurements | 20 | 150 | 200 | 220 | — |
| background current (µA) | 2 | 7 | 8 | 8 | 15 |

In Table 9, the number of times of feasible measurements means the number of times 90% or more cell efficiency was obtained in successive measurements of 10 µl of 1×10$^{-4}$M NADH as a sample. The background current indicates a faint current flowing in the coulomb meter when the galvanic cell is attached thereto. This background current is caused, for example, by a capacitive current resulting from the electroactive substance in a cell. This causes noises in measurement and interferes with accurate analysis. In a usual measurement, an S/N ratio within 1% is required for accuracy. To satisfy this requirement, the background current should be less than 10 µA in this experiment.

As can be seen from the above results, each of the upper and lower felts preferably has a top surface area of 7±3 cm$^2$ and a volume of 3.5±1.5 ml. In the range below the lower limits, because the amount of sample injected as well as the number of times of successive measurements are limited, durability deteriorates. On the other hand, in the range above the upper limits, background current increases causing a lowering of measurement accuracy, thereby resulting in poor dispersibility of a solution, high resistance, and thus poor cell efficiency. A cell efficiency of 50% or less causes at least 1% S/N ratio, and is thus not preferable with respect to reproducibility and errors in measurement. An analytical device by a galvanic cell generally requires a cell efficiency of at least 50%, preferably at least 80%. In the preferable range of the present example (i.e., the upper and lower felts each having a top surface area of 7±3 cm$^3$ and a volume of 3.5±1.5 ml), cell efficiency is preferably at least 80% in order to achieve accurate measurements.

[Example 16]

NADH was measured under the same conditions as in Example 2, using a similar galvanic cell as in Example 13 wherein upper felt 9 (20 mm diameter) was provided on its periphery with a filter paper (Filter Paper No. 2 with an inner periphery diameter of 20 mm and an outer periphery diameter of 40 mm, manufactured by Advantech Co., Ltd.). As a result, the time required for each measurement could be reduced by use of filter paper, and good results could consistently be obtained on 300 or more repeated measurements without exchanging the working electrode.

Various publications, including but not limited to certain Japanese Industrial Standards are cited herein, the disclosures of which are incorporated herein in their entirety by reference.

The entire disclosures of Japanese priority applications Nos. 290156/1992 filed Oct. 28, 1992, 30928/1993 filed Feb. 19, 1993, 163606/1993 filed Jul. 1, 1993, and 222527/1993 filed Sep. 9, 1993 are incorporated herein in their entirety by reference.

What is claimed is:

1. A method for coulometric analysis for quantitative determination of a sample substance, comprising the steps of:
    providing a first electrode with a first substance having quinol formed from a reaction between the sample substance, which is a substrate of a quinone-dependent dehydrogenase, and quinone in the presence of quinone-dependent dehydrogenase, wherein the first substance is electroactive;
    providing a second electrode with a second substance, wherein the second substance is electroactive;
    providing an ion-permeable membrane between the first and second electrodes;
    measuring an electrical property generated by a potential difference from at least one reaction between the first and second substances without application of an external power source; and
    determining the quantity of said sample substance from the measure of the electrical property.

2. The method according to claim 1, wherein the sample substance is ethyl alcohol and the quinone-dependent dehydrogenase is alcohol dehydrogenase.

3. The method according to claim 1, wherein the sample substance is glucose and the quinone-dependent dehydrogenase is glucose dehydrogenase.

4. The method according to claim 1, wherein the sample substance is fructose and the quinone-dependent dehydrogenase is fructose dehydrogenase.

5. The method according to claim 1, wherein the sample substance consists of sucrose, glucose and fructose, and total sugar content of the sample substance is quantitatively determined by using quinone-dependent glucose dehydrogenase and fructose dehydrogenase in the presence of invertase.

6. The method according to claim 1, wherein the quinone is ubiquinone derivative represented by the following formula:

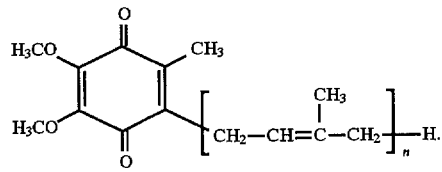

(n is an integer of 0 tp 10)

7. A method for coulometric analysis for quantitative determination of a sample substance, comprising the steps of:
    providing a first electrode with a first substance having quinol formed from a reaction between the sample substance, which is a substrate of a quinone-dependent dehydrogenase, and quinone in the presence of quinone-dependent dehydrogenase, wherein the first substance is electroactive;
    providing a second electrode with a second substance, wherein the second substance is electroactive;
    providing an ion-permeable membrane between the first and second electrodes;
    measuring an electrical property generated by a potential difference from at least one self-driven reaction between the first and second substances; and
    determining the quantity of said sample substance from the measure of the electrical property.

8. The method according to claim 7, wherein the sample substance is ethyl alcohol and the quinone-dependent dehydrogenase is alcohol dehydrogenase.

9. The method according to claim 7, wherein the sample substance is glucose and the quinone-dependent dehydrogenase is glucose dehydrogenase.

10. The method according to claim 7, wherein the sample substance is fructose and the quinone-dependent dehydrogenase is fructose dehydrogenase.

11. The method according to claim 7, wherein the sample substance consists of sucrose, glucose and fructose, and total sugar content of the sample substance is quantitatively determined by using quinone-dependent glucose dehydrogenase and fructose dehydrogenase in the presence of invertase.

12. The method according to claim 7, wherein the quinone is ubiquinone derivative represented by the following formula:

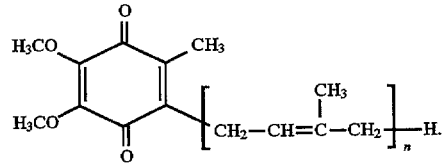

(n is an integer of 0 tp 10)

13. An apparatus for coulometric analysis for quantitative determination of a sample substance, comprising:
    a first electrode with a first substance having quinol formed from a reaction between the sample substance, which is a substrate of a quinone-dependent dehydrogenase, and quinone in the presence of quinone-dependent dehydrogenase, wherein the first substance is electroactive;

a second electrode with a second substance, wherein the second substance is electroactive;

an ion-permeable membrane situated between the first and second electrodes;

means for measuring an electrical property generated by a potential difference from at least one reaction between the first and second substances without application of an external power source; and means for determining the quantity of the sample substance from the measure of the electrical property.

14. The apparatus according to claim 13, wherein the sample substance is ethyl alcohol and the quinone-dependent dehydrogenase is alcohol dehydrogenase.

15. The apparatus according to claim 13, wherein the sample substance is glucose and the quinone-dependent dehydrogenase is glucose dehydrogenase.

16. The apparatus according to claim 13, wherein the sample substance is fructose and the quinone-dependent dehydrogenase is fructose dehydrogenase.

17. The apparatus according to claim 13, wherein the sample substance consists of sucrose, glucose and fructose, and total sugar content of the sample substance is quantitatively determined by using quinone-dependent glucose dehydrogenase and fructose dehydrogenase in the presence of invertase.

18. The apparatus according to claim 13, wherein the quinone is ubiquinone derivative represented by the following formula:

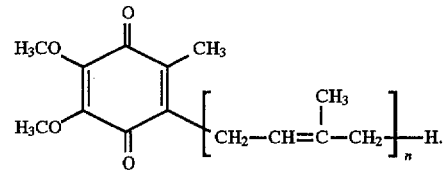

(n is an integer of 0 tp 10)

* * * * *